United States Patent
Nishida et al.

(10) Patent No.: US 9,796,605 B2
(45) Date of Patent: Oct. 24, 2017

(54) POLYMERIC IRON CHELATING AGENT

(75) Inventors: Yuzo Nishida, Ishikawa (JP); Yutaka Kohgo, Hokkaido (JP); Katsuya Ikuta, Hokkaido (JP); Katsunori Sasaki, Hokkaido (JP)

(73) Assignees: DISEASE ADSORPTION SYSTEM TECHNOLOGIES CO., LTD., Ishikawa (JP); NATIONAL UNIVERSITY CORPORATION ASAHIKAWA MEDICAL UNIVERSITY, Hokkaido (JP)

( * ) Notice: Subject to any disclaimer, the term of this patent is extended or adjusted under 35 U.S.C. 154(b) by 180 days.

(21) Appl. No.: 13/979,230

(22) PCT Filed: Jan. 12, 2012

(86) PCT No.: PCT/JP2012/000153
§ 371 (c)(1),
(2), (4) Date: Jul. 11, 2013

(87) PCT Pub. No.: WO2012/096183
PCT Pub. Date: Jul. 19, 2012

(65) Prior Publication Data
US 2013/0292337 A1 Nov. 7, 2013

(30) Foreign Application Priority Data
Jan. 14, 2011 (JP) .................. 2011-006043

(51) Int. Cl.
*B01D 21/01* (2006.01)
*B03D 3/00* (2006.01)
(Continued)

(52) U.S. Cl.
CPC ............ *C02F 1/286* (2013.01); *A61K 31/722* (2013.01); *A61K 31/731* (2013.01);
(Continued)

(58) Field of Classification Search
None
See application file for complete search history.

(56) References Cited

U.S. PATENT DOCUMENTS 4,125,519 A * 11/1978 Goodman et al. ............. 528/363
4,424,346 A * 1/1984 Hall et al. ....................... 536/20
(Continued)

FOREIGN PATENT DOCUMENTS

EP 0188037 A1 7/1986
JP 61-167644 A 7/1986
(Continued)

OTHER PUBLICATIONS

International Search Report for PCT/JP2012/000153 dated Feb. 21, 2012.
(Continued)

*Primary Examiner* — Clare Perrin
(74) *Attorney, Agent, or Firm* — Pearne & Gordon LLP

(57) ABSTRACT

Disclosed is a water-insoluble polymeric iron chelating agent having a polymer backbone and an aromatic ring attached to the polymer backbone through an —NH—$CH_2$— bond, wherein the aromatic ring has one or two first functional groups in the form of hydroxyl group and one or two second functional groups located at the ortho position with respect to the first functional group; and wherein the second functional group is —OH, —COOH, or a group represented by formula (I) wherein A represents —$CH_3$, —$CH_2$—$CH_3$, —$CH_2$—$C_6H_5$, —$CH_2$—$C_5H_4N$ or —$CH_2$—COOH and B represents —$CH_2$—COOH. The water-insoluble polymeric iron chelating agent of the present invention offers the advantages of being capable of selectively chelating iron ions, particularly biologically unstable iron, and being insoluble in water, and moreover not being incorporated in metabolic processes in vivo.

14 Claims, 4 Drawing Sheets

(51) Int. Cl.

| | | |
|---|---|---|
| *C02F 1/52* | (2006.01) | |
| *B01D 15/00* | (2006.01) | |
| *B01J 20/00* | (2006.01) | |
| *C08B 37/08* | (2006.01) | |
| *C02F 1/28* | (2006.01) | |
| *C02F 1/64* | (2006.01) | |
| *A61M 1/36* | (2006.01) | |
| *A61K 31/731* | (2006.01) | |
| *A61K 31/722* | (2006.01) | |
| *C08L 5/08* | (2006.01) | |
| *C02F 1/00* | (2006.01) | |
| *B01D 21/00* | (2006.01) | |
| *C02F 1/42* | (2006.01) | |
| *B01J 49/00* | (2017.01) | |
| *C02F 1/68* | (2006.01) | |
| *C02F 101/20* | (2006.01) | |

(52) U.S. Cl.
CPC ............ *A61M 1/3687* (2013.01); *C02F 1/52* (2013.01); *C02F 1/64* (2013.01); *C08B 37/003* (2013.01); *C08L 5/08* (2013.01); *C02F 1/683* (2013.01); *C02F 2101/203* (2013.01); *C02F 2303/16* (2013.01); *C02F 2303/18* (2013.01)

(56) References Cited

U.S. PATENT DOCUMENTS

| | | | | |
|---|---|---|---|---|
| 5,049,280 | A | * | 9/1991 | Raymond ................ B01J 45/00 210/638 |
| 5,300,628 | A | * | 4/1994 | Honda .................. G03F 7/0048 210/638 |
| 5,487,888 | A | * | 1/1996 | Mandeville, III ..... A61K 31/74 424/78.01 |
| 5,777,091 | A | | 7/1998 | Kuhn et al. |
| 5,929,112 | A | * | 7/1999 | Galey .................... A61K 8/44 514/533 |
| 5,945,170 | A | * | 8/1999 | Kozak et al. ................. 427/437 |
| 6,218,432 | B1 | | 4/2001 | Galey et al. |
| 6,242,492 | B1 | | 6/2001 | Bergeron, Jr. |
| 6,465,504 | B1 | | 10/2002 | Lattmann et al. |
| 2003/0109548 | A1 | * | 6/2003 | Royt ...................... A61K 9/127 514/312 |
| 2005/0080120 | A1 | | 4/2005 | Lattmann et al. |
| 2006/0110446 | A1 | | 5/2006 | Deffez et al. |
| 2006/0128805 | A1 | | 6/2006 | Shah |
| 2007/0274945 | A1 | * | 11/2007 | Scott .................... A61K 31/785 424/78.27 |
| 2008/0312302 | A1 | | 12/2008 | Beauchamp et al. |
| 2011/0189779 | A1 | | 8/2011 | Kohg et al. |

FOREIGN PATENT DOCUMENTS

| | | |
|---|---|---|
| JP | 6-128321 A | 5/1994 |
| JP | 8-225601 A | 9/1996 |
| JP | H9-501144 A | 2/1997 |
| JP | 2000-506546 A | 5/2000 |
| JP | 2000-507601 A | 6/2000 |
| JP | 2002-502816 A | 1/2002 |
| JP | 2004-203820 A | 7/2004 |
| JP | 2005-509649 A | 4/2005 |
| JP | 2006-504748 A | 2/2006 |
| JP | 2007-532509 A | 11/2007 |
| JP | 2008-520669 A | 6/2008 |
| JP | 2010-31022 A | 2/2010 |
| WO | 9411338 A1 | 5/1994 |
| WO | 2009/130604 A2 | 10/2009 |
| WO | 2010/032489 A1 | 3/2010 |

OTHER PUBLICATIONS

Communication—Supplementary European Search Report issued in corresponding European Patent Application No. 12734667.4, dated Jun. 5, 2014.

\* cited by examiner

POLYMERIC IRON CHELATING AGENT

CROSS-REFERENCES TO RELATED APPLICATIONS

The present application claims priority from Japanese Patent Application No. 2011-006043 (filed on Jan. 14, 2011), the contents of which are incorporated herein by reference.

TECHNICAL FIELD

The present invention relates to a water-insoluble polymeric iron chelating agent that is capable of selectively chelating biologically unstable iron, is insoluble in water, and is not incorporated in metabolic processes in vivo, as well as to a method for capturing iron ions using the chelating agent.

BACKGROUND ART

A new disease concept, referred to as chronic kidney diseases (CKD), has been proposed in recent years and this concept has attracted attention throughout the world. In order to treat the disease, the reduction or removal of biologically unstable iron (referred to as non-transferrin-bound iron or NTBI), which is the most frequent causation of the CKD, has been clearly determined to be effective. As used herein, the biologically unstable iron (NTBI) refers to iron ion that is not bound to transferrin and has the potential to have a detrimental effect on the body. Thus, biologically unstable iron (NTBI) does not include, for example, iron-bound to transferrin (iron ions present in transferrin-iron complex: transferrin-bound iron), storage iron present as ferritin in the liver, spleen and bone marrow, hemoglobin composed of four heme molecules (porphyrin complex containing iron) and one molecule of globin (comprised of four polypeptide chains) contained in erythrocytes, and myoglobin present in muscle in the form of a chromoprotein that contains a single heme molecule and is stored until oxygen molecules are required for metabolism. Examples of treatment methods for reducing iron in the body, particularly biologically unstable iron (NTBI), or for removing iron outside the body include (1) phlebotomy therapy, (2) low-iron diet therapy, (3) chemotherapy using an iron chelating agent, and (4) blood purification therapy by extracorporeal blood circulation. Phlebotomy therapy is associated with a favorable patient quality of life (QOL), however, since it involves the removal of whole blood, including erythrocytes, it causes adverse side effects such as anemia or hypoproteinemia and can only be applied to patients without anemia. Low-iron diet therapy involves reducing absorption of iron from the digestive tract. It is associated with adverse side effects such as nutritional imbalance, and is only adapted for certain types of liver diseases. Various types of iron chelating agents having potent chemotherapeutic effect have been proposed and mainly used for patients with post-transfusion iron overload (see JP A 2010-31022, WO2009/130604, JP A 2007-532509, JP A 2006-504748, JP A 2005-509649, JP A 2000-507601, JP A 2008-520669, JP A 2002-502816, JP A 2000-506546, JP A 2004-203820, and JP A H9-501144). In iron-related diseases in some organs caused by mild iron overload or iron metabolism abnormalities, there said to be a high frequency of adverse side effects attributable to over-chelation. Moreover, iron chelating agents administered to the body will possibly be incorporated in metabolic processes in vivo, thereby causing an undesirable effect on the body, such as nephropathy. In the case of blood purification therapy by extracorporeal blood circulation, since iron is removed only when blood is circulated outside the body for treatment, there is less likelihood of the occurrence of adverse side effects attributable to over-chelation. The inventors of the present invention have developed an iron chelating agent capable of selectively removing biologically unstable iron (NTBI) which can be used in blood purification therapy (see WO 2010/32489). Even in the case of the iron chelating agent capable of selectively removing biologically unstable iron (NTBI) described in WO 2010/32489, the iron chelating agent dissolved in water will potentially be incorporated into blood and integrated into the metabolic processes in vivo, resulting in an undesirable effect on the body in the same manner as the previously described chelating agents.

JP A H9-501144 describes insolubilized iron-binding polymers that have the effect of lowering absorption of food-derived heme iron and free iron from the gastrointestinal tract. In all of the polymers disclosed in JP A H9-501144, the iron chelating sites are attached to the polymer through —CO—NH— (acrylamide) bond. The iron chelating sites will be lost due to hydrolysis when the polymers are used for extracorporeal blood circulation and come in direct contact with blood, resulting in the potential for having an undesirable effect on the body. In addition, a material for removing heme iron is used in blood purification therapy by extracorporeal blood circulation, there is a high likelihood of inducing anemia, and as such, these polymers are considered to be undesirable.

Patent Document 1: JP A 2010-31022
Patent Document 2: WO 2009/130604
Patent Document 3: JP A 2007-532509
Patent Document 4: JP A 2006-504748
Patent Document 5: JP A 2005-509649
Patent Document 6: JP A 2000-507601
Patent Document 7: JP A 2008-520669
Patent Document 8: JP A 2002-502816
Patent Document 9: JP A 2000-506546
Patent Document 10: JP A 2004-203820
Patent Document 11: JP A H9-501144
Patent Document 12: WO 2010/32489

DISCLOSURE OF THE INVENTION

An object of the present invention is to provide a water-insoluble polymeric iron chelating agent that is capable of selectively chelating iron ions, and particularly biologically unstable iron (NTBI), is insoluble in water, and is not incorporated in metabolic processes in vivo, where the polymer backbone and iron chelating sites are joined by a stable chemical bond. Another object of the present invention is to provide a method for capturing iron ions using the polymeric iron chelating agent of the present invention.

As a result of conducting extensive studies to achieve the above-described objects, the inventors have found that a water-insoluble polymeric iron chelating agent wherein a phenol-based chelating agent having a specific structure is attached to a polymer chain through a stable chemical —NH—CH$_2$— bond, is able to selectively chelate iron ions and effectively capture iron ions such as biologically unstable iron (NTBI) without being incorporated in metabolic processes in vivo due to its nature of water-insolubility, thereby completed the present invention.

The present invention relates to a water-insoluble polymeric iron chelating agent, a preparation process thereof, a method for capturing iron ions using the water-insoluble polymeric iron chelating agent of the present invention, and a method for regenerating the polymeric iron chelating agent. More specifically, the present invention provides the following:

[1] a water-insoluble polymeric iron chelating agent having a polymer backbone and an aromatic ring attached to the polymer backbone through an —NH—CH$_2$— bond, wherein the aromatic ring has one or two first functional groups in the form of hydroxyl group and one or two second functional groups located at the ortho position with respect to at least one of the first functional group; and wherein the second functional group is —OH, —COOH or a group represented by the following formula (I):

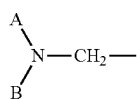

(I)

wherein A represents —CH$_3$, —CH$_2$—CH$_3$, —CH$_2$—C$_6$H$_5$, —CH$_2$—C$_5$H$_4$N or —CH$_2$—COOH and B represents —CH$_2$—COOH;

[2] the water-insoluble polymeric iron chelating agent described in [1], wherein the polymer backbone is chitosan;

[3] the water-insoluble polymeric iron chelating agent described in [1] or [2], wherein the chelated iron ions are biologically unstable iron (NTBI);

[4] a preparation process of the water-insoluble polymeric iron chelating agent described in [1], comprising the steps of forming a Schiff base by reacting an amino group on the polymer backbone with an aldehyde group of an aromatic compound, and reducing the Schiff base to form an —NH—CH$_2$— bond between the polymer backbone and the aromatic compound;

[5] the preparation process of the water-insoluble polymeric iron chelating agent described in [4], wherein the polymer backbone having an amino group is chitosan;

[6] a method for removing iron ions from an aqueous solution containing iron ions, comprising the steps of adding the polymeric iron chelating agent described in any one of [1] to [3] to an aqueous solution containing iron ions to form an iron complex, and removing the iron complex from the aqueous solution;

[7] the method described in [6], wherein the iron ions are biologically unstable iron (NTBI); and

[8] the method described in [6] or [7], further comprising the steps of adding an acid of between 0.01 N and 1.0 N to the iron complex to remove the iron ions and recovering the polymeric iron chelating agent.

The polymeric iron chelating agent of the present invention is able to selectively chelate iron ions, particularly biologically unstable iron (NTBI). In addition, since the polymeric iron chelating agent is water-insoluble, there is an extremely low possibility of it being incorporated in metabolic processes in vivo. The polymeric iron chelating agent of the invention also features in that it can be easily separated by centrifugation after having chelated iron ions in a sample. In addition, it may be reused as an iron ion chelating agent after having removed the bound iron ions.

PREFERRED EMBODIMENTS OF THE INVENTION

The polymeric iron chelating agent of the present invention has a polymer backbone and an aromatic ring attached to the polymer backbone through an —NH—CH$_2$— bond, wherein the aromatic ring has one or two first functional groups in the form of hydroxyl group and one or two second functional groups that are —OH, —COOH or a group represented by the following formula (I):

wherein, A represents —CH$_3$, —CH$_2$—CH$_3$, —CH$_2$—C$_6$H$_5$, —CH$_2$—C$_5$H$_4$N or —CH$_2$—COOH and B represents —CH$_2$—COOH. The second functional groups are located at the ortho position with respect to at least one of the first functional groups.

In a preferred embodiment, the iron chelating site comprises an aromatic ring having two hydroxyl groups located at the ortho position, and coordinate bonds are formed so that a five-membered chelate ring including an iron ion is formed.

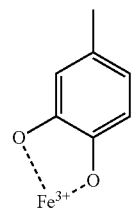

Figure 1:
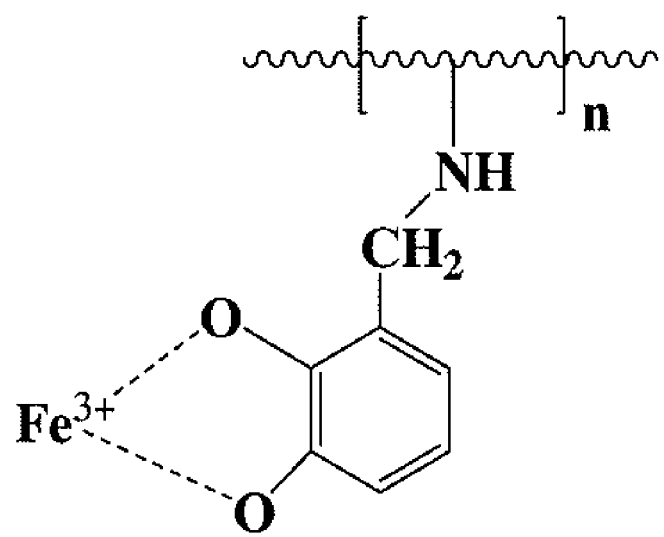
FIG. 1 shows the iron chelating structure of the polymeric iron chelating agent of the present invention.

FIG. 1 shows the structure of a polymeric iron chelating agent having such an iron chelating site. In the drawing, the wavy line indicates the polymer backbone. Examples of types of polymer backbones include linear and branched backbones, those having a side chain or side chains, and those having a three-dimensional network structure. Typically n represents an integer, and is preferably 100 to 2,000,000, more preferably 1,000 to 1,000,000, and even more preferably 2,000 to 1,000,000, although it is difficult to define the structure because some polymers cannot be dispersed or dissolved in a solvent and thus cannot be measured.

In another preferred embodiment, the iron chelating site comprises an aromatic ring having one hydroxyl group and one carboxyl group located at the ortho position, and coordinate bonds are formed so that a stable, six-membered chelate ring including an iron ion is formed.

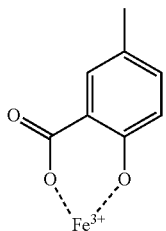

In still another preferred embodiment, the iron chelating site comprises an aromatic ring having one hydroxyl group and a functional group located at the ortho position, and is capable of chelating biologically unstable iron (NTBI) with a stable coordinate structure formed with both the five- and six-membered chelate rings. An example is represented by the following formula (II).

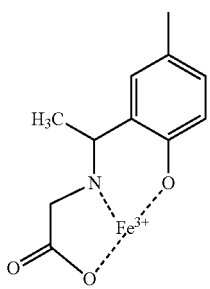

(II)

In still another preferred embodiment, the iron chelating site comprises an aromatic ring having one hydroxyl group and two functional groups represented by formula (I) positioned at the ortho position on both sides thereof, and is capable of cheleting increased amount of iron ions per chelating agent. An example is represented by the following formula (III).

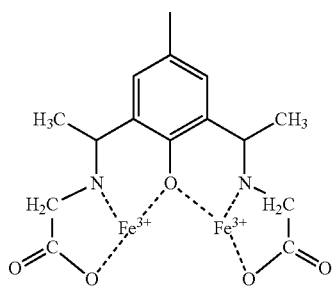

(III)

The polymer backbone represents a polymer molecule that is able to function as a carrier by forming a covalent bond with an aromatic ring that acts as an iron chelating site, and may include any types of polymers provided that it is insoluble in water. Examples of polymer backbones preferably used in the present invention include (1) known water-insoluble polymers such as polyethylene, polypropylene, polystyrene, polyvinylidene fluoride, polytetrafluoroethylene or polyethylene terephthalate, (2) water-soluble polymers having an amino group such as poly(allylamine) or polyethyleneimine capable of being insolubilized by crosslinking, and (3) water-insoluble natural polymers having a primary amine group.

In the polymeric iron chelating agent of the present invention the polymer backbone is attached to an aromatic ring through an —NH—CH$_2$— bond, wherein the aromatic ring has one or two first functional groups in the form of hydroxyl group and one or two second functional groups, such as —OH, —COOH or a group represented by formula (I), wherein the second functional groups are located at the ortho position with respect to at least one of the first functional groups. As a result of the polymer backbone and aromatic ring being joined directly through an —NH—CH$_2$— bond, the hydrolysis resistance of the —NH—CH$_2$— bond is greater than that of an —NH—CO— bond or —CO—O— bond. Moreover, the —NH—CH$_2$— bond is more preferable than —CH$_2$— or —CH$_2$—CH$_2$— bond, since it allows a polymeric chelating agent to be uniformly generated in a hydrophilic solvent compatible with the polymeric chelate.

In order to prepare the water-insoluble polymeric iron chelating agent of the present invention, amino groups may be first introduced into the polymer backbone or a polymer backbone carrying amine groups may be prepared. Amino groups can be introduced into a known water-insoluble polymer such as polyethylene, polypropylene, polystyrene, polyvinylidene fluoride, polytetrafluoroethylene or polyethylene terephthalate using a known reaction method such as a graft reaction, condensation reaction or Friedel-Crafts reaction. In addition, a water-soluble polymer carrying amino groups such as a poly(allylamine) or polyethyleneimine can be insolubilized without disturbing the iron chelating site by a crosslinking reaction before or after introducing the chelating site. Moreover, a water-insoluble natural polymer having a primary amine group such as chitosan may also be used. Chitosan is particularly preferable since it is insoluble in water, and it contains numerous primary amine groups available for the introduction of iron chelating sites through an —NH—CH$_2$— bond (i.e. providing a large number of primary amine groups per unit weight of polymer).

Next, the above-described polymer, either having amine groups or into which amine groups have been inserted, is reacted with an aldehyde derivative of the aromatic ring serving as an iron chelating site to obtain a Schiff base, then the Schiff base is reduced to form an —NH—CH$_2$— bond between the polymer backbone and aromatic ring. The aldehyde derivative of the aromatic ring is a compound that has an aldehyde group at the position of the aromatic ring where the polymer is to be attached.

The water-insoluble polymeric iron chelating agent of the present invention may be prepared, for example, in the manner described below.

1) An amino group on chitosan is reacted with an aldehyde group of 2,3-dihydroxybenzaldehyde by reacting chitosan with 2,3-dihydroxybenzaldehyde in a mixed solvent consisting of 5% acetic acid and methanol to form a Schiff base. Sodium borohydride is slowly added to the resulting gelatinous solution until the Schiff base is reduced and a crystalline precipitate is formed. From this reaction, a polymeric iron chelating agent is obtained that has chitosan and an aromatic ring attached through —NH—CH$_2$— bond (view from the chitosan side) where the aromatic ring is capable of chelating iron and has two hydroxyl groups located at the ortho positions.

2) A polymeric iron chelating agent capable of capturing two iron ions with two five-membered rings and two six-membered rings may be prepared by employing N,N'-(2-hydroxy-5-formyl-1,3-dixylene)bis(N-(methyl)-glycine) in place of 2,3-dihydroxy-benzaldehyde in the process 1) above (which can be synthesized by reacting para-hydroxybenzaldehyde and N-methylglycine in an aqueous formaldehyde solution according to the method described in Bruce P. Murch, et al., J. Am. Chem. Soc., 1985, 107 (23), pp. 6728-6729) (see formula (III)).

The polymeric iron chelating agent of the present invention can be used particularly preferably to remove biologically unstable iron (NTBI). In the present invention, biologically unstable iron (NTBI) refers to iron ions that are not bound to transferrin and have the potential to have a detrimental effect on the body. Thus, biologically unstable iron (NTBI) does not include iron bound to transferrin (iron ions present in transferrin-iron complex: transferrin-bound iron), storage iron present as ferritin in the liver, spleen and bone marrow, hemoglobin composed of four heme molecules (porphyrin complex containing iron) and one molecule of globin (comprised of four polypeptide chains) contained in erythrocytes, and myoglobin present in muscle in the form of a chromoprotein that contains a single heme molecule and is stored until oxygen molecules are required for metabolism. The iron ions in biologically unstable iron (NTBI) is normally not in a free state in vivo, but rather is thought to be in the form of chelates with amino acids or peptides including several anions. Examples of anions include a hydroxyl ion (OH—) or citric acid anion (Cit) in the form of, for example, $Fe^{3+}.3(OH^-)$ or $(FeCitOH^-)$.

The polymeric iron chelating agent of the present invention is coordinated with iron ions to form a complex (iron complex or iron chelate), which has a characteristic absorption wavelength (absorbance wavelength) that differs from the absorbance wavelength of iron ions and polymeric iron chelating agents.

More specifically, the capacity of chelating iron ions can be measured by, for example, adding the polymeric iron chelating agent of the present invention to a solution containing iron ions, and comparing colors of the polymeric iron chelating agent before and after the chelate reaction.

Solvents used for preparing a solution containing iron ions or for a washing solution (solution for transforming from the dry state to the wet state) or suspension of the polymeric iron chelating agent may include Dulbecco's phosphate-buffered saline (D-PBS(−)) or pure water (such as so-called "Milli-Q water" produced by the "Milli-Q" ultrapure water purification system manufactured by Millipore Corporation). One type of solvent may be used or two or more types may be used in combination.

The present invention provides a method for capturing iron ions characterized in that iron ions are captured by using the polymeric iron chelating agent of the present invention. The polymeric iron chelating agent of the present invention has an extremely high chelating capacity with respect to the trivalent iron ions, and is able to selectively capture iron ions and thus effectively reduce the amount of iron ions in a system. In addition, since the method allows to effectively capture iron ions in the form of biologically unstable iron (NTBI), it is possible to effectively capture excess iron in the body in the form of biologically unstable iron (NTBI), thereby reducing detrimental effects on the body caused by excess iron. Furthermore, the polymeric iron chelating agent of the present invention is also able to capture and release excess iron outside the body.

More specifically, the method for capturing iron ions may be carried out either by introducing the polymeric iron chelating agent of the present invention (or a substance containing the agent) into an iron ion-containing substance, or by introducing an iron ion-containing substance into the polymeric iron chelating agent of the present invention (or substance containing the agent). An example of an iron ion-containing substance is a liquid containing iron ions, preferably an aqueous liquid substance. Substances containing the polymeric iron chelating agent may be suitably selected and may include, but not limited to, a suspension containing the polymeric iron chelating agent, water-soluble or water-degradable capsules containing the polymer iron chelating agent, and solids (such as a filter) having the polymeric iron chelating agent immobilized thereon.

In the method for capturing iron ions of the present invention, most preferably iron ions are captured directly with the polymeric iron chelating agent of the present invention. Iron ions may also be captured by first forming a complex (chelating) with another chelating agent such as nitrilotriacetic acid (NTA), hydroxyethyl ethylenediamine triacetic acid (HEDTA) or ethylenediamine tetraacetic acid (EDTA), followed by removing the iron ions from the complex (chelate) using the polymeric iron chelating agent of the present invention.

The iron chelating agent of the present invention has a low chelating capacity with respect to iron bound to transferrin (transferrin-bound iron), and hardly removes (replaces) any iron ions from transferrin-bound iron. Thus, the iron chelating agent of the present invention is able to effectively reduce excess iron in the body because it can effectively capture only biologically unstable iron (NTBI) that is not needed by the body while removes no or almost no iron ions from transferrin-bound iron that is needed by the body.

The method for capturing iron ions of the present invention can be used in medical applications and industrial applications.

The polymeric iron chelating agent of the present invention can be regenerated by removing iron ions by washing the agent with acid having a concentration of between 0.001 N and 1 N, and preferably between 0.01 N and 1 N. Preferably, the acid used for regenerating the polymeric iron chelating agent does not cause the polymeric iron chelating agent to swell, and may be selected depending on the chemical structure of the polymer backbone and the iron chelating site of the polymeric iron chelating agent.

As used herein, any aspects represented with the expression "comprising" encompass aspects represented with the expression "essentially comprising" as well as aspects represented with the expression "consisting of".

The contents of all patents and reference documents explicitly cited in the specification are incorporated herein by reference in its entirety.

EXAMPLES

The following description provides a more detailed explanation of the present invention by way of examples, but the present invention is not limited in any way to those examples.

Example 1

700 mg of chitosan (NACALAI TESQUE, INC., derived from crab shells) and 300 mg of 5-formylsalicylic acid (Tokyo Chemical Industry Co., Ltd.) were added to a mixed solvent consisting of 50 ml of 5% acetic acid and 50 ml of methanol. 3 g of sodium borohydride (NACALAI TESQUE, INC.) were gradually added to the resulting gelatinous solution until a crystalline precipitate formed. Once the precipitate formation was ceased, the precipitation was filtered by suction and washed with methanol. After drying the product, it was further subjected to vacuum drying to obtain 700 mg of a polymeric iron chelating agent (PC-Carb2). The chemical formula of PC-Carb2 is shown below. On the basis of the feed ratio, ½ of the amino groups on chitosan are estimated to have been reacted with 5-formyl-salicylic acid and substituted with the chelate.

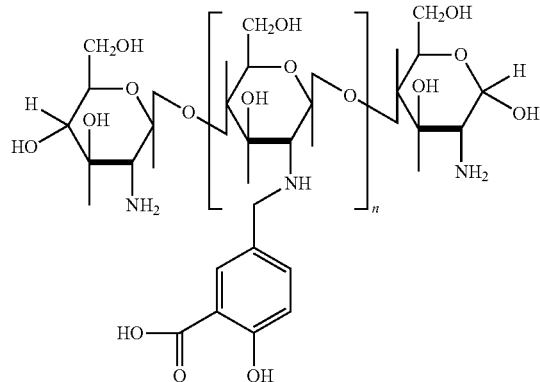

Example 2

The same procedure as Example 1 was carried out using 500 mg of the chitosan of Example 1 and 300 mg of 2,3-dihydroxybenzaldehyde (Tokyo Chemical Industry Co., Ltd.) in place of 5-formylsalicyclic acid to obtain 700 mg of polymeric iron chelating agent (PC-Cate1) in the form of a crystalline precipitate. The chemical formula of PC-Cate1 is shown below. On the basis of the feed ratio, ½ of the amino groups on chitosan are estimated to have been reacted with 2,3-dihydroxybenzaldehyde and substituted with the chelate.

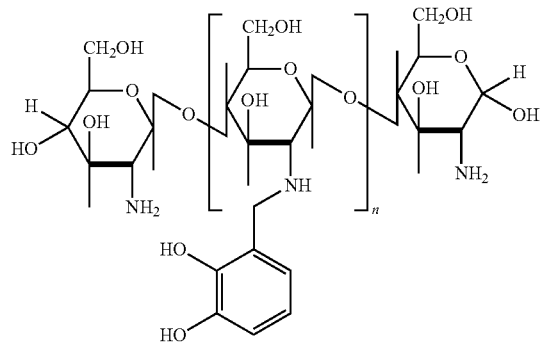

Example 3

A polymeric iron chelating agent (PC-Carb1) was obtained in the form of a crystalline precipitate according to Example 1 by using 5-methyl-3-formylsalicylic acid in place of 5-formylsalicylic acid. The chemical formula of PC-Carb1 is shown below. On the basis of the feed ratio, ½ of the amino groups on chitosan are estimated to have been reacted with 5-methyl-3-formylsalicylic acid and substituted with the chelate.

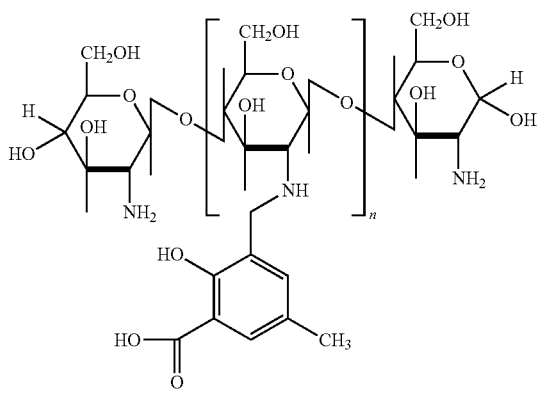

Example 4

A polymeric iron chelating agent (PC-Cate2) was obtained in the form of a crystalline precipitate according to Example 2 by using 3,4-dihydroxybenzaldehyde in place of 2,3-dihydroxybenzaldehyde The chemical formula of PC-Cate2 is shown below. On the basis of the feed ratio, ½ of the amino groups on chitosan are estimated to have been reacted with 3,4-dihydroxybenzaldehyde and substituted with the chelate.

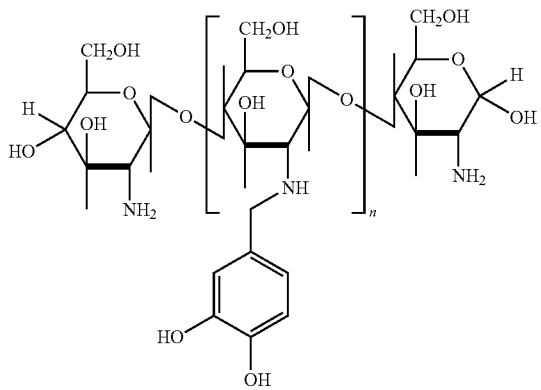

Example 5

N,N'-(2-hydroxy-5-formyl-1,3-dixylene)bis(N-methyl-glycine) was synthesized according to the method described in the reference cited above using p-hydroxybenzaldehyde (Tokyo Chemical Industry Co., Ltd.), N-methylglycine (NACALAI TESQUE, INC.) and 30% formaldehyde aqueous solution. The same procedure as Example 1 was carried out using 700 mg of the chitosan of Example 1 and 300 mg of the synthesized N,N'-(2-hydroxy-5-formyl-1,3-dixylene) bis(N-methyl-glycine) in place of 5-methyl-3-formylsalicylic acid to obtain 800 mg of a polymeric iron chelating agent (PC-Disa) in the form of a crystalline precipitate. The chemical formula of PC-Disa is shown below. On the basis of the feed ratio, ½ of the amino groups on chitosan are estimated to have been reacted with N,N'-(2-hydroxy-5-formyl-1,3-dixylene)bis(N-methyl-glycine) and substituted with the chelate.

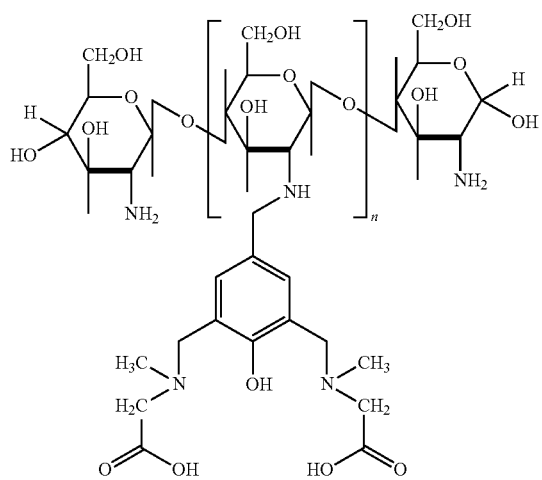

Example 6

The same procedure as Example 1 was carried out using 500 mg of the chitosan of Example 1 and 300 mg of 2,3,4-trihydroxybenzaldehyde (Tokyo Chemical Industry Co., Ltd.) in place of 5-methyl-3-formylsalicyclic acid to obtain 700 mg of a polymeric iron chelating agent (PC-Cate3) in the form of a crystalline precipitate. The chemical formula of PC-Cate3 is shown below. On the basis of the feed ratio, ½ of the amino groups on chitosan are estimated to have been reacted with 2,3,4-trihydroxybenzaldehyde and substituted with the chelate.

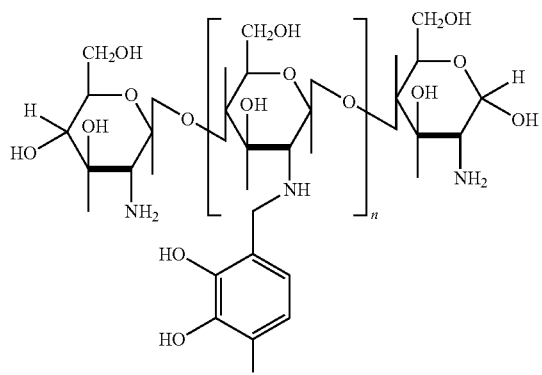

Example 7

2,4-dihydroxy-3-formylbenzene-1-N-(carboxymethyl) glycine was synthesized according to the reference cited above (Bruce P. Murch, et al., J. Am. Chem. Soc., 1985, 107(23), pp. 6728#8211; 6729) using 2,4-dihydroxybenzaldehyde, iminodiacetic acid and formaldehyde as starting materials. The same procedure as Example 1 was carried out by using 300 mg of 2,4-dihydroxy-3-formylbenzene-1-N-(carboxymethyl)glycine in place of 5-methyl-3-formylsalicyclic acid in Example 1 to obtain 700 mg of a polymeric iron chelating agent (PC-Caim1) in the form of a crystalline precipitate. The chemical formula of PC-Caim1 is shown below. On the basis of the feed ratio, ½ of the amino groups on chitosan are estimated to have been reacted with 2,4-dihydroxy-3-formylbenzene-1-N-(carboxymethyl)glycine and substituted with the chelate.

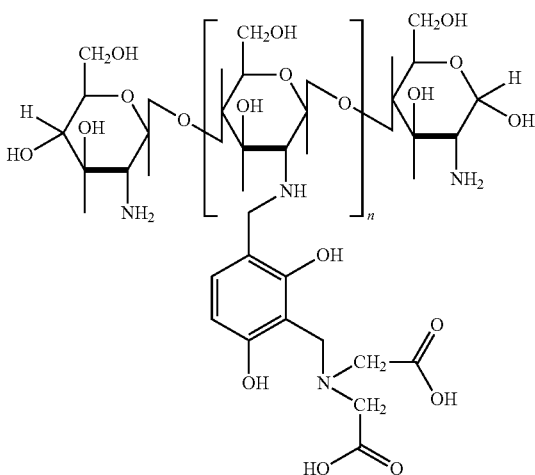

Comparative Example 1

Nitrilotriacetic acid (NTA) disodium salt (NTA2Na, trade name: "245-02", NACALAI TESQUE, INC.) and trisodium salt (NTA3Na, trade name: "245-03", NACALAI TESQUE, INC.) were used as iron chelating agents.

Comparative Example 2

Citric acid (citric acid anhydrous, trade name: "091-09", NACALAI TESQUE, INC.) was used as an iron chelating agent.

Comparative Example 3

Hydroxyethyl ethylenediamine triacetic acid (HEDTA) trisodium salt (HEDTA3Na, trade name: "H2378-100G", Sigma-Aldrich Co. LLC.) was used as an iron chelating agent.

[Polymeric Iron Chelating Agent Evaluation A]

The presence or absence of the capacity to chelate iron was evaluated according to the following evaluation method A.

(Polymeric Iron Chelating Agent Preparation Method: Wet Method)

Approximately 20 mg of polymeric iron chelating agent (air-dried sample) was weighted into a 14 ml tube, and 5 ml of Dulbecco's phosphate-buffered saline (D-PBS(−), trade name: "045-2975", Wako Pure Chemical Industries, Ltd.) were added and stirred gently for 30 minutes at room temperature to wash the polymeric iron chelating agent, then D-PBS(−) was discarded. The washing procedure was repeated three times to prepare a polymeric iron chelating agent in a wet state.

TABLE 1

| Polymeric Iron Chelating Agent | Weight in wet state corresponding to 1 mg in dry state |
|---|---|
| PC-Carb2 | 3.75 mg wet/mg dry |
| PC-Cate1 | 5.50 mg wet/mg dry |

(Citrate-Iron Complex Solution Preparation Method)

5 ml of 0.1 M citric acid solution (pH 5.91) and 28 ml of iron standard solution (Fe 100, trade name: "091-03851", Wako Pure Chemical Industries, Ltd., iron concentration:

1.78 mM Fe) were mixed and adjusted the pH of the solution to 7.0 with 4 N sodium hydroxide, then added Milli-Q water to a total volume of 50 ml. The pH of the dark yellow solution was 7.29. The final concentration of citric acid with respect to a final concentration of 1 mM of iron ions is 10 mM, thus the molar ratio of iron to citric acid is 1:10.

(Evaluation Method A)

The wet polymeric iron chelating agents of PC-Carb2 and PC-Cate1 were added at 3.75 mg and 5.50 mg (equivalent to 1 mg in the dry state), respectively, to 100 µl of citrate-iron complex solution and incubated for 30 minutes at room temperature and under protection from light. The change in color of the polymeric iron chelating agents was then monitored. When PC-Carb2 was added to the citrate-iron complex solution, a reddish-orange precipitate formed. When the chelating agent was added to citric acid solution or D-PBS not containing iron ions, the color did not change. In addition, when PC-Cate1 was added to the citrate-iron complex solution, a blackish-brown precipitate formed, while when the chelating agent was added to citric acid solution or D-PBS not containing iron ions, the color did not change.

These results show that the two types of polymeric iron chelating agents of the invention have the capacity to draw iron ions from citrate-iron complex.

In addition, the polymeric iron chelating agents of Examples 3 to 7 were shown to have the capacity to similarly draw iron ions from citrate-iron complex.

Next, the potential for reusing the polymeric iron chelating agent of the present invention was investigated. A polymeric iron chelating agent completely incorporating iron ions (black, Fe-Cate3, 500 mg) was decolored when added to 50 ml of 0.5 N hydrochloric acid solution (forming precipitate of a light brown color). At this time, swelling of the regenerated Fe-Cate3 was not observed. When the agent was filtered once and again immersed in citrate-iron complex solution, a blackish-brown precipitate formed. Incorporation and release of iron ions were able to be repeated 4 to 5 times in this manner.

[Polymeric Iron Chelating Agent Evaluation B]

In the above experiments, the polymeric iron chelating agent was shown to have the effect of removing iron ions from a low molecular weight complex (i.e. citrate-iron complex). The cheleting agent is also required to have very little effect or no effect of removing iron from transferrin-iron complex (transferrin-iron complex in which transferrin has chelated iron ions). Therefore, the polymeric iron chelating agent was evaluated as to whether it has the capacity to remove iron ions from transferrin-iron complex.

(Iron Chelating Agent Solution Preparation)

An 800 mM solution of the iron chelating agent according to Comparative Example 3 in the form of HEDTA was prepared. 13.76 g of crystals were placed in a 50 ml conical tube, and dissolved in 25 ml of Milli-Q water. The pH was adjusted to 7.0 with concentrated hydrochloric acid (35% to 37%), then added Milli-Q water to a total volume of 50 ml (800 mM HEDTA solution). 50 mM HEDTA solution was prepared in D-PBS(−) (50 mM HEDTA solution).

(Nitrilotriacetic Acid Solution Preparation)

800 mM solutions (pH 7.0) were prepared using the iron chelating agents NTA2Na and NTA3Na according to Comparative Example 1. 9.4 g of NTA2Na were dissolved in Milli-Q water and brought to a total volume of 50 ml (800 mM NTA2Na solution). On the other hand, 11.0 g of NTA3Na were dissolved in Milli-Q water and brought to a total volume of 50 ml (800 mM NTA3Na solution). The NTA2Na solution (800 mM, pH 6.3) and the NTA3Na solution (800 mM, pH 11.3) were then mixed to prepare an 800 mM NTA solution of pH 7.0. A 50 mM NTA solution (50 mM NTA solution) was then prepared using D-PBS(−).

(Transferrin-Iron Complex Preparation)

A commercially available transferrin-iron complex (holo-Transferrin (hTf), human, code: T0665-100MG, Lot: 038K1350, Sigma-Aldrich Co. LLC.) was dissolved in D-PBS(−) to prepare a 50 µM hTf solution. At this time, the concentration of iron bound to transferrin was 100 µM equal to twice the hTf concentration.

(Evaluation Method B)

50 µl of the 50 µM hTf solution was placed in a 1.5 ml sample tube and 50 µl aliquots of each of the iron chelating agent solutions (HEDTA solution (50 mM) and NTA solutions (50 mM)) were added and allowed to stand for 30 minutes at room temperature and under protection from light. 50 µl of each of the reaction solutions was taken into a centrifugal ultrafiltration unit (trade name: "UFC8030", Millipore Corporation), and 450 µl of D-PBS(−) was added and centrifuged for 1 hour at 3,000 rpm and 20° C. to separate the low molecular weight iron chelating agents from transferrin (1st round). The filtrate was discarded after centrifugation. 450 µl of D-PBS (−) were again added to the concentrated transferrin-containing solution in the unit (approximately 50 µl residue) and centrifuged under the same conditions (2nd round). After the second round of centrifugation, the concentrated transferrin-containing solution in the unit was collected and absorbance of the solution was measured at a wavelength of 466 nm (maximum absorption wavelength of hTf) with a spectrophotometer (trade name: "DU640 Spectrophotometer", Beckmann Coulter, Inc.). In the case of the polymeric iron chelating agents, 100 µl of the 50 µM hTf solution was placed in a 1.5 ml sample tube and the wet polymeric iron chelating agents in the form of 7.5 mg of PC-Carb2 (equivalent to 2 mg in the dry state) or 11.0 mg of PC-Cate1 (equivalent to 2 mg in the dry state) was added and incubated for 30 minutes at room temperature under protection from light. The mixture was centrifuged for 1 minute at 15,000 rpm and 20° C., and supernatant containing transferrin was collected. Absorbance was measured with a spectrophotometer at the maximum absorption wavelength of hTf. The evaluation results are shown in Tables 2 and 3.

TABLE 2

|  | Holo-Transferrin (hTf) | Iron chelating agent | Absorbance (466 nm) | Residual ratio of hTf (%) |
|---|---|---|---|---|
| Baseline (D-PBS) | (−) | (−) | (−) |  |
| Non-treated | (+) | (−) | 0.0713 | 100.0 |
| Example 1 | (+) | PC-Carb2 | 0.0700 | 98.1 |
| Example 2 | (+) | PC-Cate1 | 0.0653 | 91.5 |

TABLE 3

|  | Holo-Transferrin (hTf) | Polymeric iron chelating agent | Absorbance (466 nm) | Residual ratio of hTf (%) |
|---|---|---|---|---|
| Baseline (D-PBS) | (−) | (−) | (−) |  |
| Non-treated | (+) | (−) | 0.0631 | 100.0 |
| Comp. Ex. 3 | (+) | HEDTA | 0.0477 | 75.6 |
| Comp. Ex. 1 | (+) | NTA | 0.0468 | 74.2 |

As shown in Table 2, the polymeric iron chelating agents according to the Examples demonstrated little change in absorbance (466 nm) when added to a transferrin-iron complex solution, indicating that the agent removed almost no iron ions from the transferrin-iron complex.

[Polymeric Iron Chelating Agent Evaluation C]

An additional study was conducted to examine whether NTBI in blood can be removed by pretreating serum with the polymeric iron chelating agent. A modified version of the conventional method (subtraction method) was used to measure NTBI. The sample was divided into two aliquots: one aliquot was used as a sample [A] for measuring total iron concentration containing background iron concentration, the other aliquot was used as a sample [B] for measuring the background iron concentration. The iron concentrations of each sample were determined, and net iron concentration (NTBI) was determined by subtracting background iron concentration [B] from total iron concentration [A].

(Sample Pretreatment)

Figure 2:
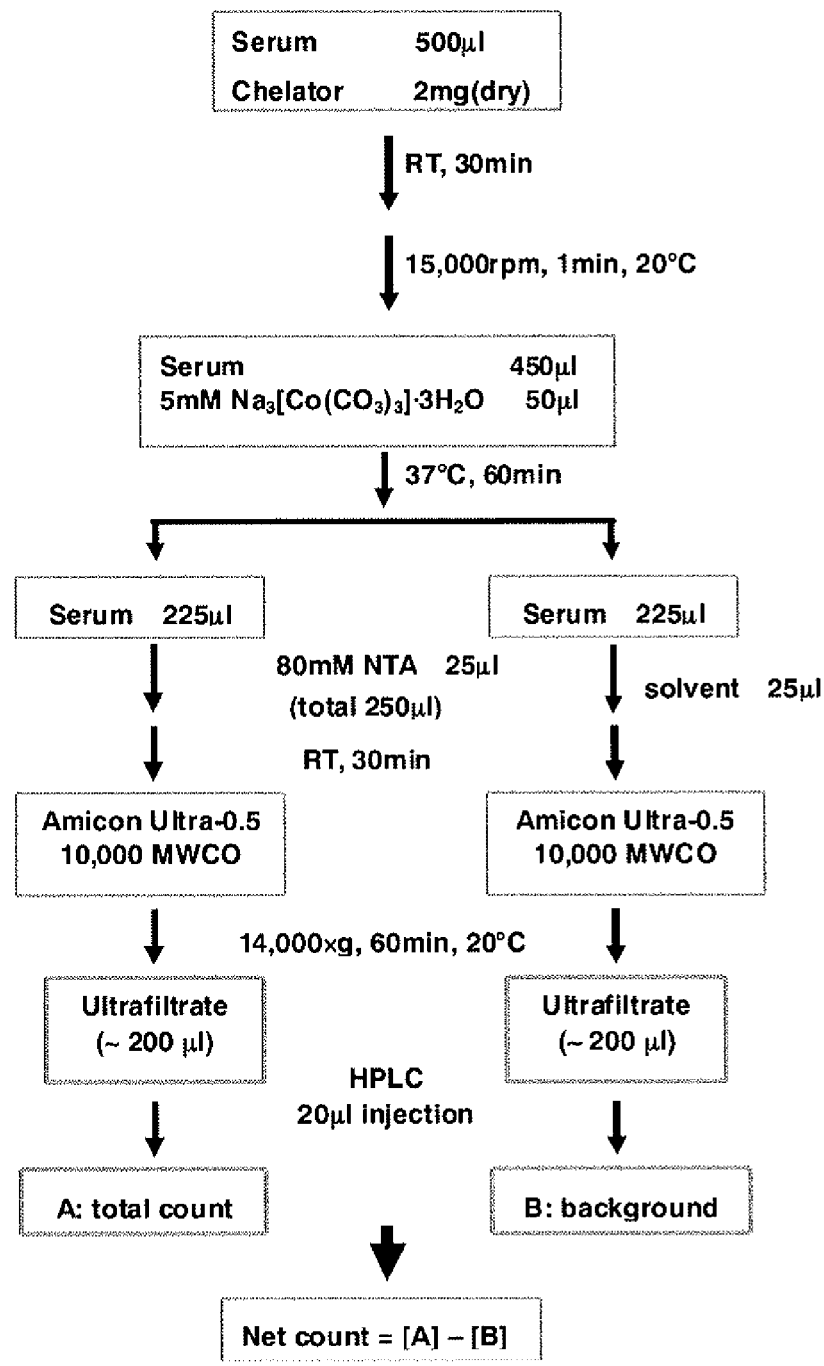
FIG. 2 shows a sample pretreatment method for measuring NTBI.

The method used for sample pretreatment is shown in FIG. 2. A frozen stored sample (serum) was rapidly thawed and stored refrigerated on ice until use. 500 µl of the thawed sample were taken into a 1.5 ml sample tube then the wet polymeric iron chelating agent: 11.0 mg of PC-Cate1 or 7.5 mg of PC-Carb2 (equivalent to 2 mg in the dry state) was added and incubated for 30 minutes at room temperature. The supernatant serum was collected by centrifugation for 1 minute at 15,000 rpm and 20° C. 450 µl of the supernatant were taken into a fresh 1.5 ml sample tube and 50 µl of 5 mM [Na $Co(CO_3)_3$].$3H_2O$ was added. After allowing to stand in a constant temperature bath at 37° C., cobalt ions were introduced at the iron binding sites of apotransferrin. One hour later, the sample was removed from the 37° C. constant temperature bath, and 225 µl aliquots of the cobalt ion-treated sample were respectively added to two 1.5 ml sample tubes. 25 µl of the 80 mM NTA3Na solution were added to one of the sample tubes (Sample A), while 25 µl of the solvent used when preparing the 80 mM NTA3Na solution were added to the other sample tube (Sample B). After allowing to stand for 30 minutes at room temperature, non-transferrin-bound iron (NTBI) was captured as Fe-NTA complex. Next, the sample was added to an ultrafiltration unit having a cutoff molecular weight of 10,000 for the purpose of separating the Fe-NTA from iron-binding proteins present in the sample containing transferrin and ferritin along with the chromogenic protein, bilirubin. The sample was separated by centrifugation for 1 hour at 14,000×g and 20° C. to obtain a ultrafiltrate. 20 µl aliquots of each of the ultrafiltrates of Sample A and Sample B were injected into a non-metal HPLC.

Quantification of NTBI by HPLC:

Equipment: A non-metal HPLC system was constructed with Model 2796 BioSeparation Module with a non-metallic polyether-ethyl ketone (PEEK) tube and Model 2998 Photodiode Array Detector (Waters Corporation) equipped with OmniSher 5C18 glass column (G100×3 Repl., Varian, Inc.) and ChromSep Guard Column (Varian, Inc.).

Mobile phase: 5 mM MOPS (DOJINDO LABORATORIES), 3 mM CP22 (chromogenic chelating agent described in Biochemical Pharmacology, 57:1305-1310, 1999, synthesized on request), and a 20% acetonitrile solution (Wako Pure Chemical Industries, Ltd.) were prepared and subjected to filtration and degassing treatment with a filtration filter unit (Stericup & Steritop, trade name: SCHVU05RE, Millipore Corporation).

Quantification: A standard curve for calculating iron concentration over an iron concentration range of 0 µM to 10 µM was obtained by electrothermal atomic absorption spectrometry using Fe-NTA solutions of a predetermined iron concentrations. 20 µl aliquots of each of the ultrafiltrates of Sample A and Sample B were injected, iron concentration was determined from the peak corresponding to the location at which the Fe-NTA used for determining the standard curve is detected as Fe-CP22 (using 450 nm for the detector wavelength). The concentration of NTBI in the sample was calculated by subtracting the iron concentration of Sample B (background iron concentration) from the iron concentration of Sample A (total iron concentration including background). The subtraction method is illustrated in FIG. 2.

(Evaluation Method C)

Figure 3:
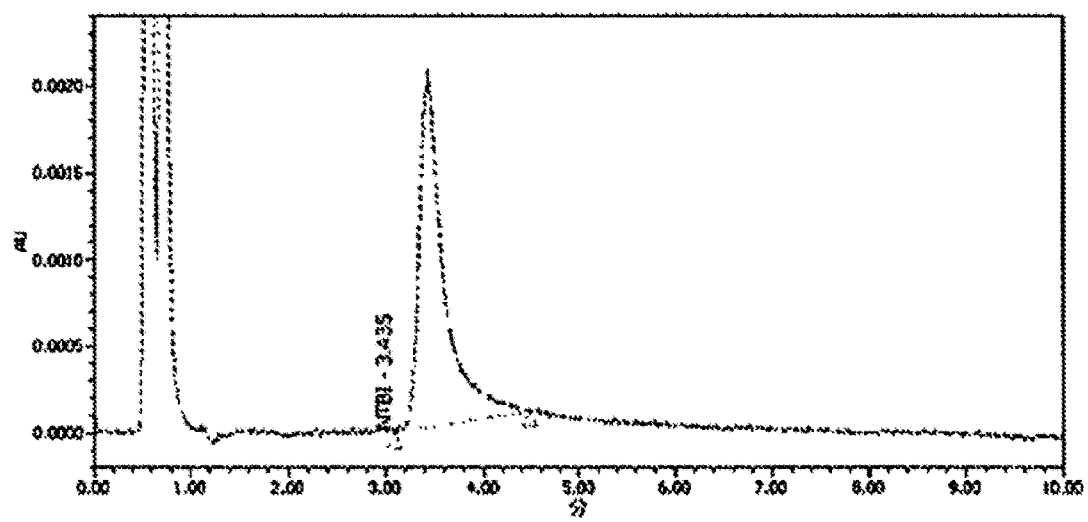
FIG. 3 shows the results of measuring NTBI in untreated serum.
Figure 4:
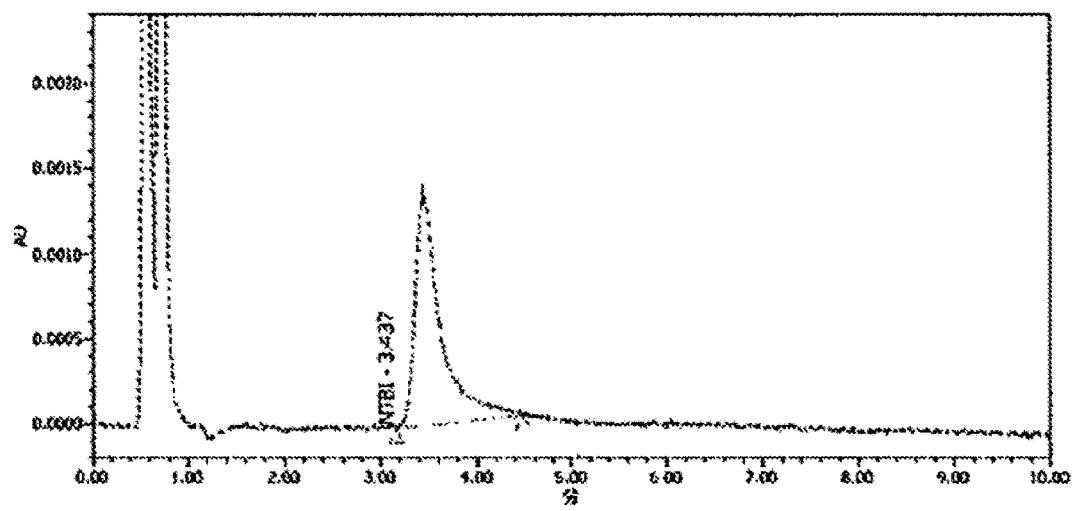
FIG. 4 shows the results of measuring NTBI in serum after having treated with a polymeric iron chelating agent PC-Carb2 of the present invention.
Figure 5:
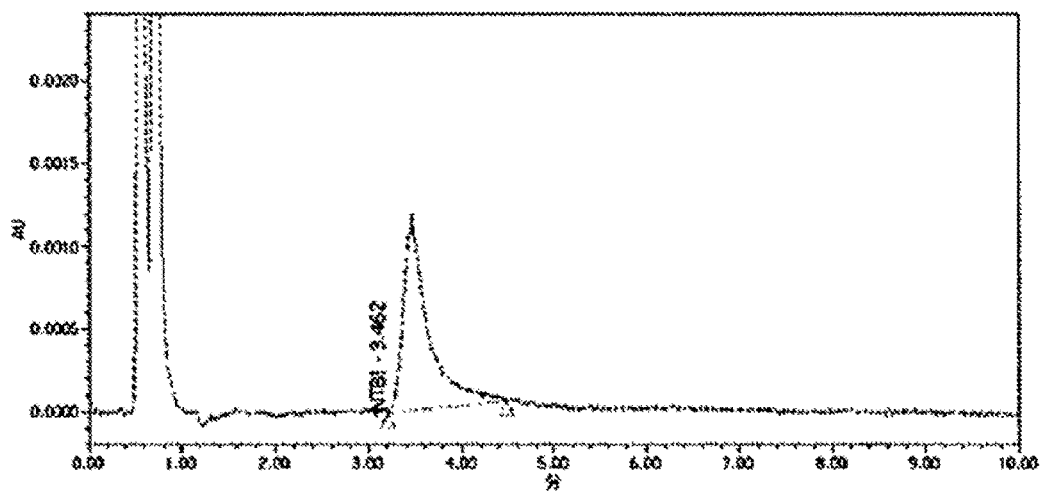
FIG. 5 shows the results of measuring NTBI in serum after having treated with a polymeric iron chelating agent PC-Cate1 of the present invention.

NTBI concentration in serum not treated with polymeric iron chelating agent was determined as a control and compared with a serum NTBI concentration after treatment with the polymeric iron chelating agent: PC-Carb2 or PC-Cate1. The NTBI concentration of untreated serum was 1.325 µM, while the NTBI concentration of serum treated with PC-Carb2 and PC-Cate1 was 0.805 µM and 0.565 µM, respectively. The HPLC detection patterns for serum NTBI are shown in FIGS. 3, 4 and 5, and the evaluation results are summarized in Table 4.

TABLE 4

| Serum | NTBI (µM Fe) | Absorption rate of NTBI by polymeric iron chelating agent |
|---|---|---|
| Non-treated | 1.325 | |
| PC-Carb2 treatment | 0.805 | 39.24% |
| PC-Cate1 treatment | 0.565 | 57.35% |

In the above experiments, serum was treated with polymeric iron chelating agent under the conditions where the polymeric iron chelating agent equivalent to 2 mg (dry weight basis) was added to 500 µl of serum and allowed to react for 30 minutes at room temperature. These results demonstrate that NTBI in the serum was able to be absorbed and removed.

INDUSTRIAL APPLICABILITY

The water-insoluble polymeric iron chelating agent of the present invention is industrially useful and offers advantages in that it is water-insoluble and hardly incorporated in metabolic processes in vivo; it has an ability to selectively chelate iron ions; in particular it captures effectively biologically unstable iron (NTBI); it may be easily separated from a sample by centrifugation; it may be regenerated by removing the bound iron ions and used repeatedly for chelating iron ions.

The invention claimed is:

1. A method for removing biologically unstable iron ions, selectively over transferrin-bound irons, from an aqueous solution containing the biologically unstable iron ions and the transferrin-bound irons, comprising the steps of adding a polymeric iron chelating agent to the aqueous solution to form an iron complex, and removing the iron complex from the aqueous solution, wherein the polymeric iron chelating agent has a polymer backbone and an aromatic ring attached to the polymer backbone directly through an —NH—CH$_2$— bond, and the polymeric iron chelating agent is water-insoluble, wherein (i) the aromatic ring has one or two first functional groups in the form of hydroxyl group and one or two second functional groups located at the ortho position with respect to at least one of the first functional group; and wherein the second functional group is —OH or a group represented by the following formula (I):

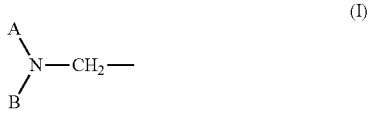

wherein A represents —CH$_3$, —CH$_2$—CH$_3$, —CH$_2$—C$_6$H$_5$, —CH$_2$—C$_5$H$_4$N or —CH$_2$—COOH and B represents —CH$_2$—COOH; or wherein (ii) the aromatic ring is represented by the formula:

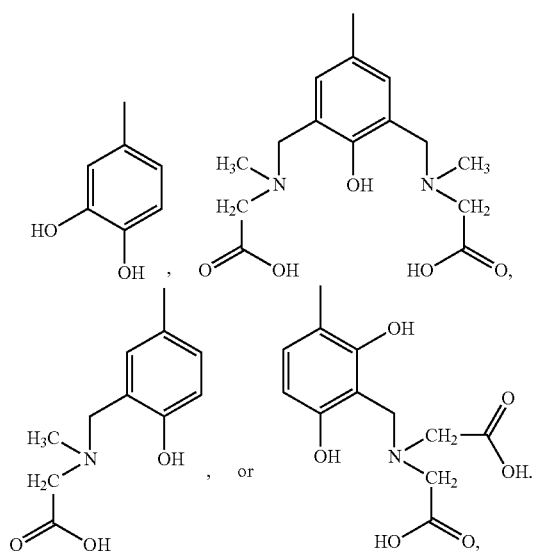

2. The method according to claim 1, further comprising the steps of adding an acid of between 0.01 N and 1.0 N to the iron complex to remove the iron ions and recovering the polymeric iron chelating agent.

3. The method according to claim 1, wherein the polymer backbone is chitosan.

4. The method according to claim 3, further comprising the steps of adding an acid of between 0.01 N and 1.0 N to the iron complex to remove the iron ions and recovering the polymeric iron chelating agent.

5. The method according to claim 3, wherein the iron complex is formed in the aqueous solution inside of a body of a human patient, in blood of the human patient, the blood comprising the aqueous solution, thereby reducing detrimental effects on the body of the human patient caused by excess iron in the blood.

6. The method according to claim 3, wherein the iron complex is formed in the aqueous solution outside of a body of a human patient, in blood of the human patient, the blood comprising the aqueous solution.

7. The method according to claim 1, wherein the aqueous solution comprises serum.

8. The method according to claim 1, wherein the iron complex is formed in the aqueous solution inside of a body of a human patient, in blood of the human patient, the blood comprising the aqueous solution, thereby reducing detrimental effects on the body of the human patient caused by excess iron in the blood.

9. The method according to claim 1, wherein the iron complex is formed in the aqueous solution outside of a body of a human patient, in blood of the human patient, the blood comprising the aqueous solution.

10. The method according to claim 1, wherein (i) the aromatic ring has one or two first functional groups in the form of hydroxyl group and one or two second functional groups located at the ortho position with respect to at least one of the first functional group; and wherein the second functional group is —OH or a group represented by the following formula (I):

wherein A represents —CH$_3$, —CH$_2$—CH$_3$, —CH$_2$—C$_6$H$_5$, —CH$_2$—C$_5$H$_4$N or —CH$_2$—COOH and B represents —CH$_2$—COOH.

11. The method according to claim 1, wherein (ii) the aromatic ring is represented by the formula:

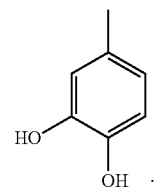

12. The method according to claim 1, wherein (ii) the aromatic ring is represented by the formula:

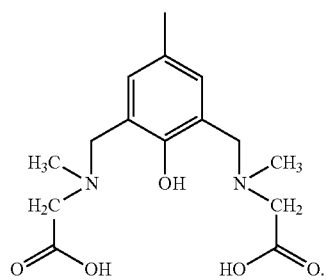 [SMILES: Cc1cc(CN(C)CC(=O)O)c(O)c(CN(C)CC(=O)O)c1]

13. The method according to claim 1, wherein (ii) the aromatic ring is represented by the formula:

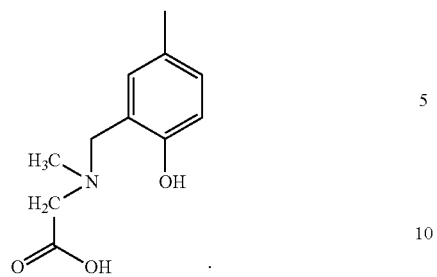
14. The method according to claim 1, wherein (ii) the aromatic ring is represented by the formula:
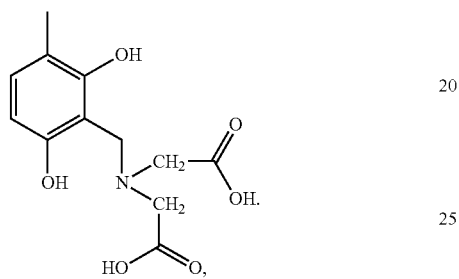
* * * * *